United States Patent
Yamasaki et al.

(10) Patent No.: US 11,415,569 B2
(45) Date of Patent: Aug. 16, 2022

(54) METHOD FOR DETECTING RESIDUAL CROSSLINKING AID

(71) Applicant: SUMITOMO ELECTRIC INDUSTRIES, LTD., Osaka (JP)

(72) Inventors: Satoshi Yamasaki, Osaka (JP); Kentaro Okamoto, Osaka (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 605 days.

(21) Appl. No.: 16/476,625

(22) PCT Filed: May 17, 2017

(86) PCT No.: PCT/JP2017/018490
§ 371 (c)(1),
(2) Date: Jul. 9, 2019

(87) PCT Pub. No.: WO2018/131186
PCT Pub. Date: Jul. 19, 2018

(65) Prior Publication Data
US 2019/0369079 A1 Dec. 5, 2019

(30) Foreign Application Priority Data

Jan. 10, 2017 (JP) .............................. JP2017-001635

(51) Int. Cl.
*G01N 33/44* (2006.01)
*G01N 30/88* (2006.01)

(52) U.S. Cl.
CPC ............. *G01N 33/44* (2013.01); *G01N 30/88* (2013.01)

(58) Field of Classification Search
CPC ... G01N 2030/8405; G01N 2030/8859; G01N 30/7206; G01N 30/8675;
(Continued)

(56) References Cited

U.S. PATENT DOCUMENTS

| 4,159,894 A | 7/1979 | Hu | |
| 5,191,211 A * | 3/1993 | Gorman, Jr. ............ | H01J 41/04 |
| | | | 73/23.35 |

(Continued)

FOREIGN PATENT DOCUMENTS

| JP | H11-148925 A | 6/1999 |
| JP | 2007-57506 A | 3/2007 |

(Continued)

OTHER PUBLICATIONS

Zhao Bangron, et al., "Analysis of Some Crosslinked Poly (methylemethacrylate) Materials by Pyrolysis-Gas Chromatography-Mass Spectrometry," Analytical Chemistry Research Bulletin, vol. 24, No. 9, pp. 1043-1045, Sep. 30, 1996 (concise explanation of relevance provided by attached CN Office Action and machine translation thereof).

Kazumi Nakayama et al., "Influences of the Residual Peroxide on Degradation of Crosslinked EPDM," Journal of the Society of Rubber Industry, 2007, pp. 165-171, vol. 80, No. 5, including English abstract.

*Primary Examiner* — Nimeshkumar D Patel
*Assistant Examiner* — Gedeon M Kidanu
(74) *Attorney, Agent, or Firm* — Faegre Drinker Biddle & Reath LLP

(57) ABSTRACT

A method for detecting a residual crosslinking aid in a crosslinked resin molded body includes a subject heating step in which a crosslinked resin molded body is heated at a temperature of 500° C. or higher and 700° C. or lower for a time of 3 seconds or more and 30 seconds or less, a subject analysis step in which gas chromatographic analysis is performed on a gas generated in the subject heating step, and a detection step in which an unreacted crosslinking aid is detected on the basis of a peak originating from a residual crosslinking aid in a chromatogram obtained in the subject analysis step.

4 Claims, 6 Drawing Sheets

(58) Field of Classification Search
CPC ........... G01N 2001/2229; G01N 30/06; G01N 33/445; G01N 30/88; G01N 33/44; C08J 2201/026; C08J 2203/04; C08J 2205/06; C08J 2205/10; C08J 2207/00; C08J 2323/08; C08J 2323/16; C08J 2409/06; C08J 2453/02; C08J 3/24; C08J 9/0061; C08J 9/103; C08L 2203/14; C08L 2205/025; C08L 2205/03; C08L 23/16; C08L 23/30; C08L 2312/02; C08L 9/00; H01J 41/04

See application file for complete search history.

(56) References Cited

U.S. PATENT DOCUMENTS

| | | | |
|---|---|---|---|
| 2012/0074312 A1* | 3/2012 | Iida | G01N 30/8675 |
| | | | 250/282 |
| 2018/0208723 A1* | 7/2018 | Ting | C08J 3/24 |

FOREIGN PATENT DOCUMENTS

| | | | | |
|---|---|---|---|---|
| JP | 2010-281633 A | | 12/2010 | |
| JP | 2010281633 A | * | 12/2010 | ......... G01N 30/7206 |
| JP | 2013-228240 A | | 11/2013 | |
| JP | 2013228240 A | * | 11/2013 | |

\* cited by examiner

METHOD FOR DETECTING RESIDUAL CROSSLINKING AID

TECHNICAL FIELD

The present invention relates to a method for detecting a residual crosslinking aid. The present invention is based upon and claims the benefit of priority from Japanese Patent Application No. 2017-001635, filed Jan. 10, 2017, the entire contents of which are incorporated herein by reference.

BACKGROUND ART

Molded bodies made of a resin composition having, as a main component, a crosslinked resin are used for various applications. Since various additives are added to a resin composition for the modification purpose, there has been a demand for an analysis method for determining a trace additive in a resin composition.

For example, a method has been proposed in which a mid-infrared spectrum in a mid-infrared region is measured so that a peak is produced for a trace additive in a resin composition, and on the basis of data of the mid-infrared spectrum, qualitative analysis and quantitative analysis of the trace additive in the resin composition are performed (refer to Japanese Unexamined Patent Application Publication No. 2007-57506). According to the method described in this patent application publication, it is stated that even when the amount of addition of an additive is 1% by weight or less, the additive can be measured.

CITATION LIST

Patent Literature

PTL 1: Japanese Unexamined Patent Application Publication No. 2007-57506

SUMMARY OF INVENTION

Solution to Problem

A method for detecting a residual crosslinking aid according to an embodiment of the present invention is a method for detecting a residual crosslinking aid in a crosslinked resin molded body, the method including a subject heating step in which a crosslinked resin molded body is heated at a temperature of 500° C. or higher and 700° C. or lower for a time of 3 seconds or more and 30 seconds or less, a subject analysis step in which gas chromatographic analysis is performed on a gas generated in the subject heating step, and a detection step in which an unreacted crosslinking aid is detected on the basis of a peak originating from a residual crosslinking aid in a chromatogram obtained in the subject analysis step.

DESCRIPTION OF EMBODIMENTS

Figure 1:
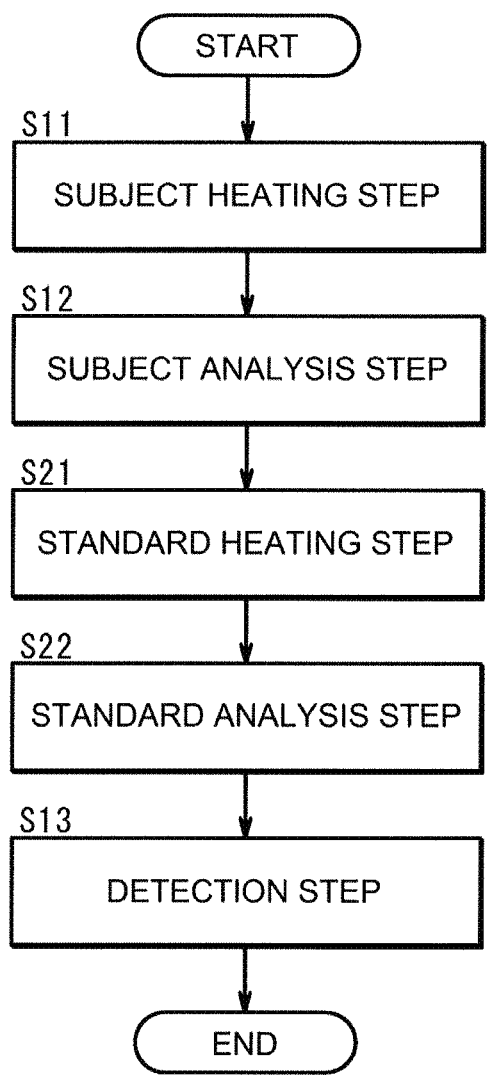
FIG. 1 is a flowchart showing a procedure of a method for detecting a residual crosslinking aid according to an embodiment of the present invention.

Problems to be Solved by the Invention

Among substances that are added to a resin composition, a crosslinking aid is incorporated into a polymer chain when the resin is crosslinked, and the residual amount thereof is very small. Therefore, even with the method according to the patent application publication described above, it is difficult to detect a very trace amount of a crosslinking aid remaining in a crosslinked resin molded body.

The present invention has been made under the circumstances as described above, and it is an object of the invention to provide a method for detecting a residual crosslinking aid which can detect a trace amount of a residual crosslinking aid in a crosslinked resin molded body.

Advantageous Effects of the Present Disclosure

A method for detecting a residual crosslinking aid according to an embodiment of the present invention can detect a trace amount of a residual crosslinking aid in a crosslinked resin molded body.

Description of Embodiments of the Present Invention

A method for detecting a residual crosslinking aid according to an embodiment of the present invention is a method for detecting a residual crosslinking aid in a crosslinked resin molded body, the method including a subject heating step in which a crosslinked resin molded body is heated at a temperature of 500° C. or higher and 700° C. or lower for a time of 3 seconds or more and 30 seconds or less, a subject analysis step in which gas chromatographic analysis is performed on a gas generated in the subject heating step, and a detection step in which an unreacted crosslinking aid is detected on the basis of a peak originating from a residual crosslinking aid in a chromatogram obtained in the subject analysis step.

In the method for detecting a residual crosslinking aid, in the subject heating step, by loosening the polymer chain network, a crosslinking aid which remains without being subjected to crosslinking is volatilized. In the subject heating step, by performing heating at a high temperature for a short time as described above, pyrolysis of the polymer is suppressed, and the proportion of a crosslinking aid in the generated gas can be increased. Accordingly, in the method for detecting a residual crosslinking aid, since it is possible to distinguish the peak of a crosslinking aid in the chromatogram obtained in the subject analysis step, a trace amount of a residual crosslinking aid can be detected.

Preferably, the crosslinking aid is a monomer or oligomer having two or more double bonds other than aromatic rings in its structure. In this way, when the crosslinking aid is a monomer or oligomer having two or more double bonds other than aromatic rings in its structure, the crosslinking aid is volatilized in the subject heating step and produces a peak in a chromatogram obtained in the subject analysis step. Therefore, the crosslinking aid can be detected by the method for detecting a residual crosslinking aid.

Preferably, the crosslinking aid is triallyl cyanurate or trimethylol propane triacrylate. In this way, when the crosslinking aid is triallyl cyanurate or trimethylol propane triacrylate, detection by the method for detecting a residual crosslinking aid becomes relatively reliable.

Preferably, the crosslinked resin molded body has, as a main component, a polyamide, polyolefin, polyester, olefin-based resin, ester-based resin, styrene-based resin, fluororesin, or vinyl chloride resin. In this way, when the crosslinked resin molded body has, as a main component, a polyamide, polyolefin, polyester, olefin-based resin, ester-based resin, styrene-based resin, fluororesin, or vinyl chloride resin, the advantage of the method for detecting a residual crosslinking aid compared with other methods becomes noticeable.

Preferably, the method for detecting a residual crosslinking aid further includes a standard heating step in which the crosslinking aid alone is heated under the same conditions as those in the subject heating step and a standard analysis step in which chromatographic analysis is performed on a gas generated in the standard heating step, in which, in the detection step, among peaks in the chromatogram obtained in the subject analysis step, a peak with a retention time equal to a retention time of a peak originating from the crosslinking aid in a chromatogram obtained in the standard analysis step is considered as the peak originating from the residual crosslinking aid. In this way, by providing the standard heating step and the standard analysis step, in the detection step, it is possible to accurately determine whether or not the peak originating from the crosslinking aid is included in the chromatogram obtained in the subject analysis step.

Here, the term "main component" means a component whose mass content is the largest. Furthermore, the expression "a retention time equal to" means that, in identification by general chromatographic analysis, the retention time is in a corresponding range.

Detailed Description of Embodiments of the Present Invention

Embodiments of the present invention will be described below.

[Method for Detecting Residual Crosslinking Aid]

FIG. 1 shows a procedure of a method for detecting a residual crosslinking aid according to an embodiment of the present invention. The method for detecting a residual crosslinking aid is a method for detecting a residual crosslinking aid in a crosslinked resin molded body.

The method for detecting a residual crosslinking aid includes a subject heating step (step S11) in which a crosslinked resin molded body is heated at a predetermined heating temperature (furnace temperature) for a predetermined heating time, a subject analysis step (step S12) in which gas chromatographic analysis is performed on a gas generated in the subject heating step S11, and a detection step (step S13) in which an unreacted crosslinking aid is detected on the basis of a peak originating from a residual crosslinking aid in a chromatogram obtained in the subject analysis step S12.

The method for detecting a residual crosslinking aid preferably further includes, as shown in FIG. 1, prior to the detection step S13, a standard heating step (step S21) in which the crosslinking aid alone that is intended to be detected is heated under the same conditions as those in the subject heating step S11, and a standard analysis step (step S22) in which chromatographic analysis is performed on a gas generated in the standard heating step S21.

<Subject Heating Step>

In step S11, i.e., the subject heating step, by heating a crosslinked resin molded body at a high temperature for a short time, a residual crosslinking aid remaining free without being incorporated into a polymer chain is detached from the crosslinked resin molded body. That is, in the subject heating step S11, by volatilizing the residual crosslinking aid and loosening the polymer chain network of the crosslinked resin molded body by heating, the residual crosslinking aid is released out of the crosslinked resin molded body.

The heating temperature in the subject heating step S11 is preferably a sufficiently high temperature, for example, a temperature equal to or higher than the pyrolysis temperature of a resin serving as a main component of the crosslinked resin molded body, so that the polymer chain network can be loosened to such an extent that the residual crosslinking aid can be detached in a short time. Furthermore, the heating time in the subject heating step S11 is preferably a short heating time to such an extent to prevent pyrolysis of most of the resin serving as a main component of the crosslinked resin molded body.

Specifically, the lower limit of the heating temperature is 500° C., and preferably 550° C. On the other hand, the upper limit of the heating temperature is 700° C., and preferably 650° C. When the heating temperature is lower than the lower limit, there is a concern that it may not be possible to release the residual crosslinking aid. Contrarily, when the heating temperature is higher than the upper limit, there is a concern that the polymer component of the crosslinked resin molded body may be pyrolyzed, thereby decreasing accuracy of detection of the residual crosslinking aid.

Furthermore, the specific lower limit of the heating time is 3 seconds, preferably 6 seconds, and more preferably 10 seconds. On the other hand, the upper limit of the heating time is 30 seconds, preferably 20 seconds, and more preferably 15 seconds. When the heating time is less than the lower limit, there is a concern that it may not be possible to release the residual crosslinking aid. Contrarily, when the heating time is more than the upper limit, there is a concern that the polymer component of the crosslinked resin molded body may be pyrolyzed, thereby decreasing accuracy of detection of the residual crosslinking aid.

<Subject Analysis Step>

In step S12, i.e., the subject analysis step, a gas generated in the subject heating step S11 is subjected to chromatographic separation with a gas chromatograph. Furthermore, in the subject analysis step S12, preferably, mass spectrometric analysis (mass spectrometry) is performed on the gas subjected to chromatographic separation at the same time.

By performing mass spectrometric analysis in the subject analysis step S12, it is possible to confirm that a peak extracted in the detection step S13, which will be described later, originates from a residual crosslinking aid. Note that since the gas generated in the subject heating step S11 contains various types of pyrolysis gas of polymer components of the crosslinked resin molded body, there are extremely many peaks in the chromatogram. Accordingly, it is very complicated to determine a peak originating from a residual crosslinking aid by checking the individual mass spectrometric analysis results (mass spectrum) of these many peaks. Therefore, it is realistic to use the mass spectrometric analysis results as a verification means.

<Standard Heating Step>

In step S21, i.e., the standard heating step, a sample of a crosslinking aid alone that is intended to be detected is heated under the same conditions as those in the subject heating step S11.

<Standard Analysis Step>

In step S22, the standard analysis step, gas chromatographic analysis is performed on a gas generated in the standard heating step S21 under the same conditions as those in the subject analysis step S12 as much as possible (with the same analyzer, the same column type used, and the same set parameters).

In this way, by using the same gas chromatographic analysis conditions, in the detection step S13, which will be described later, it is possible to accurately determine the retention time of the peak originating from the crosslinking aid among many peaks in the chromatogram obtained in the subject analysis step S12.

In the standard analysis step S22, it is also preferable to perform mass spectrometric analysis in order to confirm that a peak in the chromatogram corresponds to the peak originating from the crosslinking aid. Supposing the case where the molecular weight calculated from the mass spectrum of the peak in the chromatogram is different from the molecular weight of the crosslinking aid, it is considered that parameters, such as heating temperature and heating time, in the gas chromatographic analysis are not adequately set. Therefore, it is preferable to reset the parameters and to carry out the steps S11 to S22 again.

<Detection Step>

In step S13, i.e., the detection step, among peaks in the chromatogram obtained in the subject analysis step S12, a peak with a retention time equal to a retention time of a peak originating from the crosslinking aid alone in a chromatogram obtained in the standard analysis step S22 may be considered as the peak originating from the residual crosslinking aid.

Furthermore, among peaks in the chromatogram obtained in the subject analysis step S12, a peak with a retention time close to a retention time of a peak originating from the crosslinking aid alone in a chromatogram obtained in the standard analysis step S22 may be extracted, and by checking a mass spectrum in the subject analysis step S12 at the retention time of this peak, it may be confirmed whether or not this peak is the peak originating from the residual crosslinking aid.

<Crosslinked Resin Molded Body>

The crosslinked resin molded body, in which a residual crosslinking aid is detected by the method for detecting a residual crosslinking aid, has a resin as a main component, and the resin serving as a main component is crosslinked by a crosslinking aid. Furthermore, the crosslinked resin molded body to be subjected to detection may contain a resin other than the resin serving as a main component, and may further contain various additives, such as a reinforcement, a flame retardant, and a sliding material.

As the crosslinked resin molded body, in which a residual crosslinking aid is detected by the method for detecting a residual crosslinking aid, a crosslinked resin molded body in which the degree of crosslinking of the resin is high, and it is difficult to detect a residual crosslinking aid by other methods is assumed. Specific examples thereof include injection moldings, such as connector bodies and lenses, extrusions, such as coverings for insulated electrical wires, heat-shrinkable tubings, and heat-resistant tubes, and slide members which are rubbed against other objects. Above all, slide members have a particularly high degree of crosslinking, and the method for detecting a residual crosslinking aid is suitably applied thereto. Examples of the slide members include gears, cams, bearings, and the like. Such slide members are required to have mechanical strength, in particular, abrasion resistance, and therefore, the degree of crosslinking of the resin is relatively high, and there is a high possibility that a residual crosslinking aid cannot be detected by other methods. Thus, the advantage of the method for detecting a residual crosslinking aid becomes noticeable.

(Main Component of Crosslinked Resin Molded Body)

The main component of the crosslinked resin molded body may be, for example, a polyamide, polyolefin, polyester, olefin-based resin, ester-based resin, styrene-based resin, fluororesin, or vinyl chloride resin, and may be an elastomer. In particular, in the case where the main component of the crosslinked resin molded body is a polyamide which is relatively rigid and in which it is difficult to detect a trace amount of a compound incorporated therein by other methods, the advantage of the method for detecting a residual crosslinking aid becomes noticeable.

Examples of the polyamide include polyamide 6, polyamide 66, polyamide 46, polyamide 11, polyamide 12, polyamide 610, polyamide 612, polyamide 66/6I, polyamide 66/6T, polyamide 6T/66, polyamide 6T/6I, polyamide 6T/6I/66, polyamide 6T/5MT, polyamide 6T/6, polyamide MXD-6, polyamide 9T, and wholly aromatic polyamides. Among these, in particular, the method for detecting a residual crosslinking aid is suitably used for a crosslinked resin molded body having, as a main component, polyamide 66 which has high elastic modulus and mechanical strength.

Examples of the polyolefin include polyethylenes (PE: HDPE, LLDPE, LDPE, and VLDPE), and polypropylenes (PP).

Examples of the polyester include polyethylene terephthalate (PET), polyethylene naphthalate (PEN), polytrimethylene terephthalate (PTT), and polybutylene terephthalate (PBT).

Examples of the olefin-based resin include ethylene-vinyl acetate copolymers (EVA), cyclic olefin copolymers (COC), cycloolefin polymers (COP), ethylene-methyl acrylate copolymers (EMA), ethylene-ethyl acrylate copolymers (EEA), ethylene butyl acrylate copolymers (EBA), ethylene-butene copolymers, ethylene-octene copolymers, ethylene propylene rubber (EPR), ionomer resins, and olefin-based elastomers (TPO).

Examples of the urethane-based resin include thermoplastic polyurethane elastomers (TPU).

Examples of the ester-based resin include polyester-based thermoplastic elastomers (TPEE).

Examples of the styrene-based resin include hydrogenated styrene-based thermoplastic elastomers (SEBS).

Examples of the fluororesin include polyvinylidene fluoride (PVDF) and tetrafluoroethylene-ethylene copolymers (ETFE).

Examples of the vinyl chloride resin include polyvinyl chloride (PVC).

(Crosslinking Aid)

The crosslinking aid to be detected by the method for detecting a residual crosslinking aid may be a monomer or oligomer having two or more double bonds other than aromatic rings in its structure. In this way, in the case where a monomer or oligomer having a relatively low molecular weight remains, without being subjected to crosslinking, in a crosslinked resin molded body, it can be volatilized by heating and can be detected by the method for detecting a residual crosslinking aid.

Specific examples of the crosslinking aid include an allyl compound, a (meth)acrylate compound, an oxime compound, a vinyl compound, and a maleimide compound. Note that a crosslinking aid can be used alone or two or more crosslinking aids may be used in combination.

Examples of the allyl compound include hexamethylene bisallylnadiimide, diallyl itaconate, diallyl phthalate, diallyl isophthalate, diallyl monoglycidyl isocyanurate, triallyl cyanurate, and triallyl isocyanurate. Among these, triallyl isocyanurate is more preferable.

Examples of the (meth)acrylate compound include diethylene glycol diacrylate, diethylene glycol dimethacrylate, polyethylene glycol diacrylate, polyethylene glycol dimethacrylate, trimethylol propane triacrylate, trimethylol propane trimethacrylate, ethoxylated bisphenol A diacrylate, ethoxylated bisphenol A dimethacrylate, acrylic acid/zinc oxide mixtures, allyl acrylate, allyl methacrylate, trimethacryl isocyanurate, and pentaerythritol triacrylate. Among these, trimethylol propane triacrylate is more preferable.

Examples of the oxime compound include p-quinonedioxime and p,p'-dibenzoyl quinonedioxime.

Examples of the vinyl compound include divinylbenzene.

Examples of the maleimide compound include N,N'-m-phenylene bismaleimide and N,N'-(4,4'-methylenediphenylene)dimaleimide.

Above all, as the crosslinking aid, from the standpoint that the crosslinking density of the crosslinked resin molded body can be further increased, allyl compounds and acrylate compounds are preferable, and triallyl isocyanurate and trimethylol propane triacrylate are particularly preferable. Triallyl isocyanurate and trimethylol propane triacrylate can be relatively reliably detected by the method for detecting a residual crosslinking aid.

The lower limit of the molecular weight of the crosslinking aid is preferably 180, and more preferably 220. On the other hand, the upper limit of the molecular weight of the crosslinking aid is preferably 1,000, more preferably 400, and still more preferably 300. When the molecular weight of the crosslinking aid is less than the lower limit, since crosslinking of the resin serving as a main component is weakened, there is a possibility that other detection methods can be applied, and the advantage of the method for detecting a residual crosslinking aid may be decreased in some cases. Contrarily, when the molecular weight of the crosslinking aid is more than the upper limit, it becomes necessary to increase the heating temperature or heating time during heating of the subject, and there is a concern that the resin serving as the main component may be pyrolyzed, thereby decreasing accuracy of detection.

As a reinforcement that can be incorporated into the crosslinked resin molded body, for example, an inorganic filler, such as glass fiber, wollastonite, calcium carbonate, clay, an organically layered silicate compound, silica, or talc, may be considered. By incorporating an inorganic filler into the crosslinked resin molded body, the mechanical strength of the crosslinked resin molded body can be further improved. From this viewpoint, it is considered that a needle-shaped filler is used as the inorganic filler in many cases.

Examples of a flame retardant that can be incorporated into the crosslinked resin molded body include halogen-based flame retardants, metal hydroxides, phosphorus-based flame retardants, and nitrogen-based flame retardants.

Examples of a sliding material that can be incorporated into the crosslinked resin molded body include polyethylenes, such as ultra-high molecular weight polyethylenes; polyolefins, such as polypropylenes; fluororesins, such as polytetrafluoroethylene, polytetrafluoroethylene-perfluoroalkoxy ethylene copolymers, and polytetrafluoroethylene-polyhexafluoropropylene; silicones, such as polydimethylsiloxane, polymethylphenylsiloxane, amino-modified polydimethylsiloxane, epoxy-modified polydimethylsiloxane, alcohol-modified polydimethylsiloxane, carboxy-modified polydimethylsiloxane, and fluorine-modified polydimethylsiloxane; layered inorganic compounds, such as graphite; inorganic fibers, such as glass fibers, potassium titanate whiskers, zinc oxide whiskers, and boronic acid whiskers; organic fibers, such as LCP fibers, aramid fibers, and carbon fibers; inorganic particles, such as alumina, silica and talc; phosphates, such as metaphosphate, pyrophosphate, calcium hydrogen phosphate, potassium hydrogen phosphate, barium phosphate, lithium phosphate, calcium metaphosphate, and zinc pyrophosphate; mineral oils, such as spindle oil, turbine oil, machine oil, and dynamo oil; montanates, such as calcium montanate; and molybdenum disulfide. Note that these sliding materials can be used alone or in combination of two or more thereof.

In particular, as a sliding material that is incorporated into a crosslinked resin molded body having a polyamide as a main component, it is assumed that a polyolefin is used because the abrasion resistance of the crosslinked resin molded body can be further enhanced, and typically, there is a possibility that a polyethylene may be incorporated as a sliding material.

The crosslinked resin molded body can contain other additives than the reinforcement, the flame retardant, and the sliding material, such as a polymerization inhibitor, a filler, a plasticizer, a pigment, a stabilizer, a lubricant, a softener, a sensitizer, an antioxidant, a release agent, a weathering agent, an antistatic agent, and a silane coupling agent. Note that these additives can be used alone or in combination of two or more.

<Advantages>

In the method for detecting a residual crosslinking aid, in the subject heating step S11, by heating a crosslinked resin molded body at a high temperature for a short time, a residual crosslinking aid is volatilized, and the polymer chain network is loosened so that the volatilized residual crosslinking air is released out of the crosslinked resin molded body. Therefore, in the subject analysis step S12, the proportion of the crosslinking aid in the gas subjected to gas chromatographic analysis can be relatively increased. Accordingly, in the method for detecting a residual crosslinking aid, in the detection step S13, it is possible to relatively accurately decide whether or not the peak of the crosslinking aid is present in the chromatogram obtained in the subject analysis step S12.

Moreover, in the method for detecting a residual crosslinking aid, by further providing the standard heating step S21 and the standard analysis step S22, in the detection step S13, it is possible to more accurately decide whether or not the peak originating from the crosslinking aid is included in the chromatogram of the crosslinked resin molded body.

Other Embodiments

It should be considered that the embodiment disclosed above is illustrative and non-restrictive in all aspects. The scope of the present invention is not limited to the embodiment described above but is defined by the appended claims, and is intended to include all modifications within the meaning and scope equivalent to those of the claims.

In the method for detecting a residual crosslinking aid, the standard heating step and the standard analysis step may be performed prior to the subject heating step and the subject analysis step, and in the case where a plurality of chromatographic analysers are available, the steps may be performed simultaneously. Furthermore, in the method for detecting a residual crosslinking aid, in the case where the retention time of the peak originating from the residual crosslinking aid in the chromatogram obtained in the subject analysis step can be determined on the basis of a past record or a theory, the standard heating step and the standard analysis step may be omitted.

Examples

The present invention will be described more specifically below on the basis of examples. However, it is to be understood that the present invention is not limited to the examples.

In order to verify the effects of a method for detecting a residual crosslinking aid according to the present invention, Sample 1 of a crosslinked resin molded body in which a crosslinking aid remained and Sample 2 of a crosslinked resin molded body in which a crosslinking aid did not remain were produced, and a detection test for a residual crosslinking aid was carried out.

<Sample 1>

First, 100 parts by mass of a polyamide and 1 part by mass of a crosslinking aid were mixed to obtain a resin composition. As the polyamide, "Leona (registered trade mark) 1402S" (polyamide 66) manufactured by Asahi Kasei Corporation was used, and as the crosslinking aid, "TAICROS (registered trade mark)" (triallyl isocyanurate) manufactured by Evonik Degussa GmbH was used.

Next, the resin composition was fed into a twin-screw mixer, and melt mixing was performed at 240° C. After the melt mixing process, the resin composition was discharged from the twin-screw mixer, and the discharged material was water-cooled and cut to obtain a pellet-shaped resin composition. Then, the pellet-shaped resin composition was fed into an injection molding machine, and by performing injection molding with the injection molding machine, a plate-shaped molded body of 40 mm×40 mm×2 mm was obtained. Conditions for the injection molding were as follows: injection temperature, 280° C.; mold temperature, 80° C.; injection pressure, 100 kg/cm$^2$; and holding time, 10 sec.

Next, by irradiating the plate-shaped molded body with electron beams at an irradiation dose of 120 kGy, Sample 1 was obtained.

<Sample 2>

In Sample 2, the same polyamide as that of Sample 1, without a crosslinking aid being incorporated thereinto, was cured only by electron beam irradiation.

<Sample 3>

Sample 3 was produced in the same manner as that of Sample 2, except that the content of the crosslinking aid was set at 0.5 parts by mass, and the electron beam irradiation dose was set at 600 kGy.

<Sample 4>

100 Parts by mass of a polyethylene and 1 part by mass of a crosslinking aid were mixed to obtain a resin composition. As the polyethylene, "SUMIKATHENE (registered trade mark) C215" (LDPE) manufactured by Sumitomo Chemical Company, Limited was used, and as the crosslinking aid, "TAICROS (registered trade mark)" (triallyl isocyanurate) manufactured by Evonik Degussa GmbH was used.

Next, the resin composition was fed into a twin-screw mixer, melt mixing was performed at 240° C., and then the mixture was extruded into a tube with an average inside diameter of 3 mm and an average thickness of 0.5 mm. By irradiating the tube-shaped extrusion with electron beams at an irradiation dose of 120 kGy, Sample 4 was obtained.

<Sample 5>

100 Parts by mass of an ethylene-vinyl acetate copolymer, 1 part by mass of a crosslinking aid, and 150 parts by mass of a flame retardant were mixed to obtain a resin composition. As the ethylene-vinyl acetate copolymer, "EV40LX" manufactured by DUPONT-MITSUI POLYCHEMICALS CO., LTD. was used, as the crosslinking aid, trimethylol propane triacrylate manufactured by Shin-Nakamura Chemical Co., Ltd. was used, and as the flame retardant, "KISUMA (registered trademark) 5B" manufactured by Kyowa Chemical Industry Co., Ltd. was used.

Next, the resin composition was mixed by using a pressure kneader, and the mixture was applied by extrusion coating on a single copper wire with a diameter of 0.8 mm, followed by electron beam irradiation at an irradiation dose of 120 kGy to obtain an insulated electrical wire. The coating of the insulated electrical wire was separated from the wire and used as Sample 5.

<Detection Test>

In the detection test, by using a pyrolysis gas chromatograph equipped with a mass spectrometric analyser (Py-GC/MS), a subject heating step and a subject analysis step were continuously performed on each of Sample 1 and Sample 2. Furthermore, a standard heating step and a standard analysis step were continuously performed on the crosslinking aid alone. In a detection step, by using a chromatogram obtained for each of Sample 1 and Sample 2 in the subject analysis step, and a chromatogram for the crosslinking aid alone obtained in the standard analysis step, the presence or absence of the residual crosslinking aid was determined on Sample 1 and Sample 2. In the subject analysis step and the standard analysis step, simultaneously with chromatographic analysis, mass spectrometric analysis was performed.

In the pyrolysis gas chromatograph used, a measuring apparatus body was "6890N/5973Network" manufactured by Agilent Technologies, Ltd., which was equipped with a Multi-Shot Pyrolyzer "PY-2020iD" and MicroJet Cryo-Trap "MJT-1030Ex" manufactured by Frontier Laboratories Ltd. as pyrolysis equipment. Furthermore, as a column, "UA-5" (inside diameter 0.25 mm, length 30 m, film thickness 0.25 μm) manufactured by Frontier Laboratories Ltd. was used.

The subject heating step and the standard heating step were performed under the conditions in which the heating temperature was 600° C. and the heating time was 12 seconds. Furthermore, the subject analysis step and the standard analysis step were performed under the conditions in which the injection port temperature was 300° C., the split ratio was 50:1, and the trap temperature was −150° C. The oven temperature was raised from 50° C. at a rate of 25° C./min, and the temperature was retained at 320° C. for 5 minutes. Helium was used as a carrier gas, and the column flow rate was set at 1 mL/min. The mass spectrometric analysis was performed by an electron ionization method in which the ion source temperature was set at 230° C., the quadrupole temperature was set at 150° C., and the mass measurement range was set to 33 amu or more and 550 amu or less.

Figure 2:
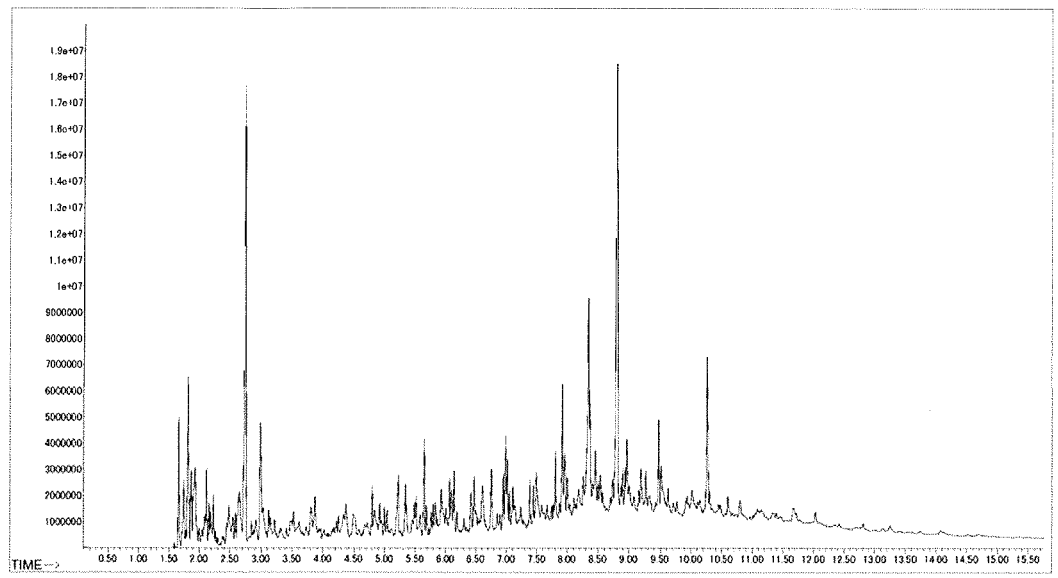
FIG. 2 is a chromatogram obtained in a subject analysis step for Sample 1.
Figure 3:
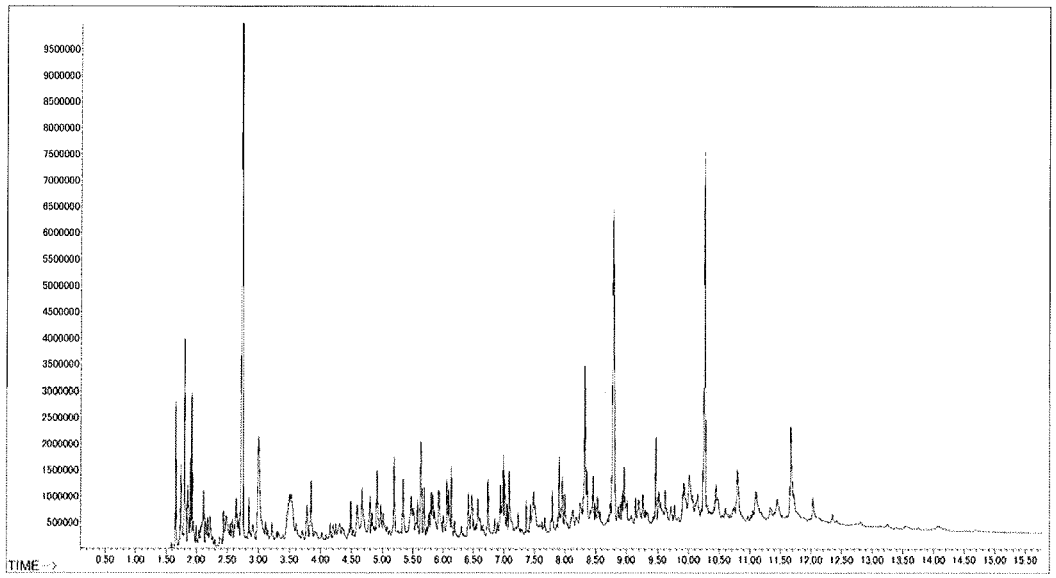
FIG. 3 is a chromatogram obtained in a subject analysis step for Sample 2.
Figure 4:
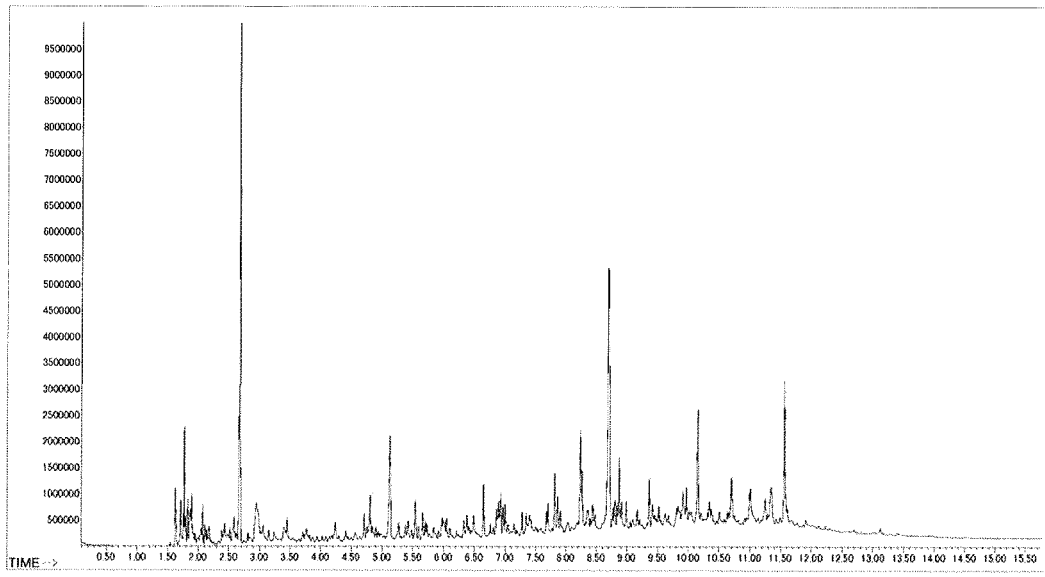
FIG. 4 is a chromatogram obtained in a subject analysis step for Sample 3.
Figure 5:
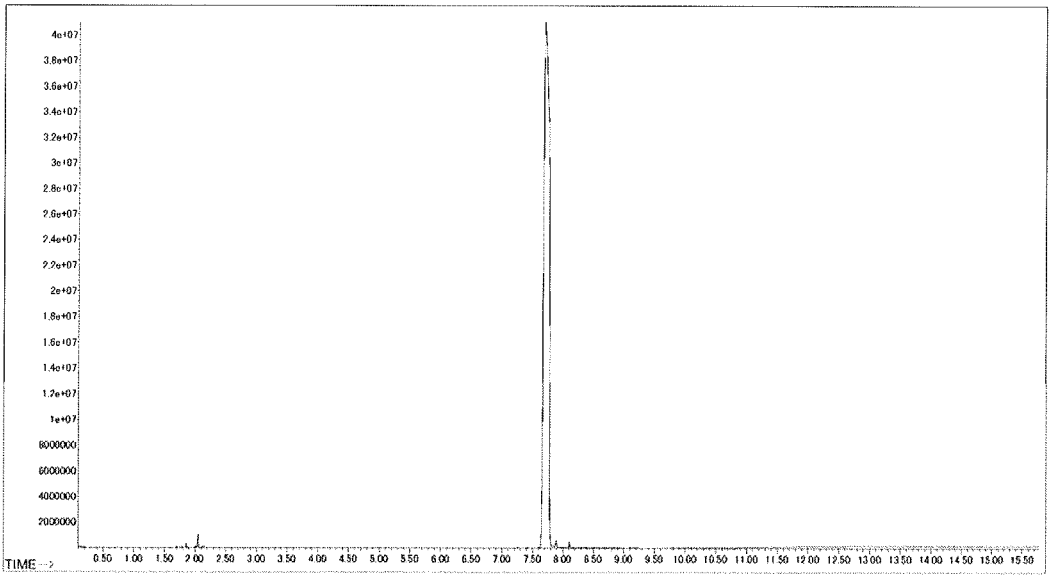
FIG. 5 is a chromatogram obtained in a standard analysis step for a crosslinking aid alone.

FIG. 2 shows a chromatogram obtained in the subject analysis step for Sample 1, FIG. 3 shows a chromatogram obtained in the subject analysis step for Sample 2, FIG. 4 shows a chromatogram obtained in the subject analysis step for Sample 3, and FIG. 5 shows a chromatogram obtained in the standard analysis step for the crosslinking aid alone.

Figure 6:
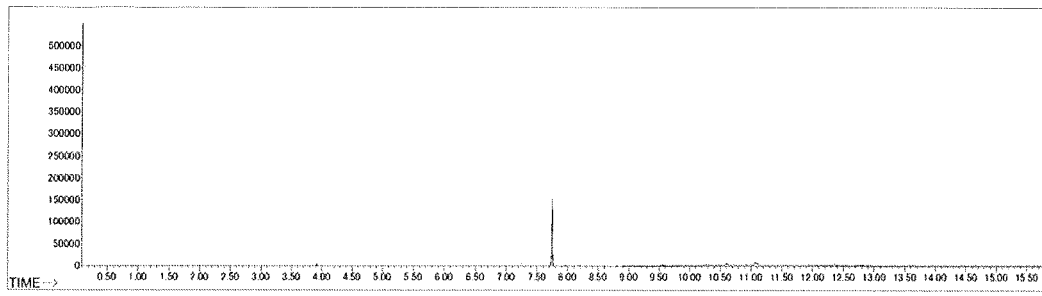
FIG. 6 is a graph showing a peak waveform originating from a residual crosslinking aid, extracted from the chromatogram shown in FIG. 2.
Figure 7:
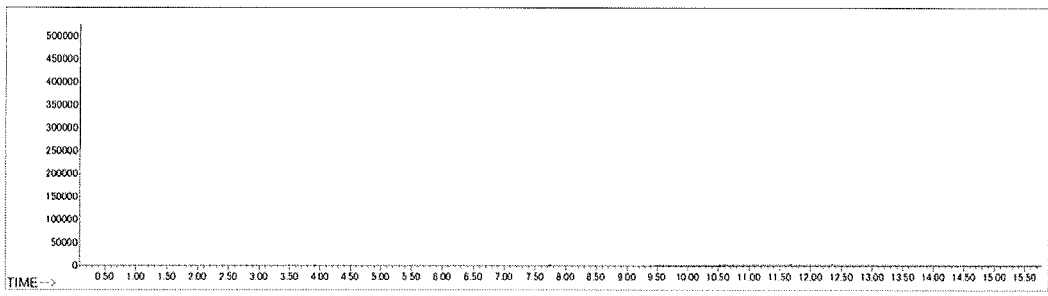
FIG. 7 is a graph showing a peak waveform originating from a residual crosslinking aid, extracted from the chromatogram shown in FIG. 3.
Figure 8:
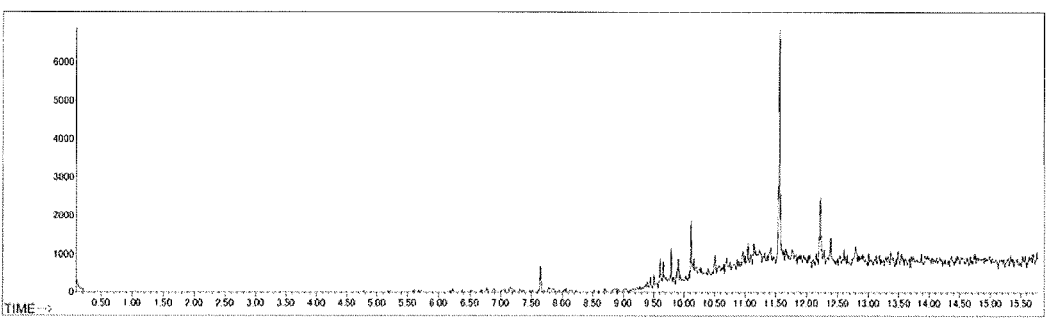
FIG. 8 is a graph showing a peak waveform originating from a residual crosslinking aid, extracted from the chromatogram shown in FIG. 4.

In the detection step, first, it was confirmed from the chromatogram for the crosslinking aid alone shown in FIG. 5 that the retention time of the peak was 7.737 min. Subsequently, the peak at the retention time of 7.737 min was extracted from each of the chromatogram for Sample 1 shown in FIG. 2, the chromatogram for Sample 2 shown in FIG. 3, and the chromatogram for Sample 3 shown in FIG. 4. FIG. 6 shows a peak at the retention time of 7.737 min, extracted from the chromatogram for Sample 1, FIG. 7 shows a peak at the retention time of 7.737 min, extracted from the chromatogram for Sample 2, and FIG. 8 shows a peak at the retention time of 7.737 min, extracted from the chromatogram for Sample 3. As shown in the graphs, the chromatogram for Sample 1 has the peak originating from the residual crosslinking aid, while the chromatogram for Sample 2 does not have the peak originating from the residual crosslinking aid. That is, it was possible to detect the residual crosslinking aid from Sample 1 only.

Figure 9:
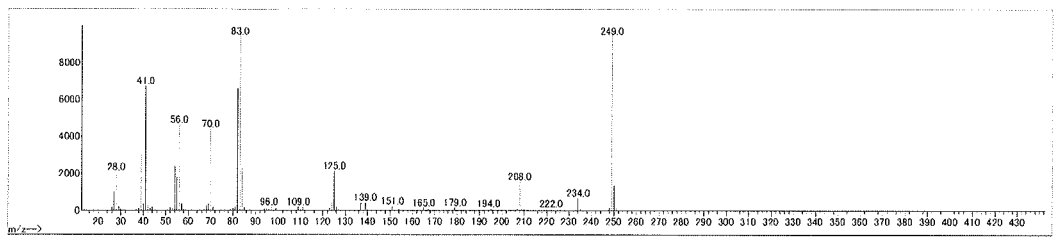
FIG. 9 shows a mass spectrum at the retention time of 7.737 min in a standard analysis step for a crosslinking aid alone.

Furthermore, in the subject analysis step, by checking the mass spectrometric analysis result at the retention time of 7.737 min, it was confirmed that the detected peak originated from the crosslinking aid. FIG. 9 shows a mass spectrum at the retention time of 7.737 min obtained in the standard analysis step, FIG. 10 shows a mass spectrum at the retention time of 7.737 min for Sample 1 obtained in the subject analysis step, and FIG. 11 shows a mass spectrum at the retention time of 7.737 min for Sample 3 obtained in the subject analysis step.

The mass spectrum for the crosslinking aid alone shown in FIG. 9 has a peak at the m/z value of 249.0. This substantially corresponds to the molecular weight (249.7) of triallyl isocyanurate used as the crosslinking aid. Therefore, the peak at the retention time of 7.737 min in the chromatogram for the crosslinking aid alone is the peak originating from triallyl isocyanurate used as the crosslinking aid. Furthermore, the mass spectrum shown in FIG. 9 also has peaks at the m/z value of 125.0, the m/z value of 83.0, the m/z value of 70.0, and the m/z value of 56.0, and these peaks are considered to correspond to decomposition products of triallyl isocyanurate.

Figure 10:
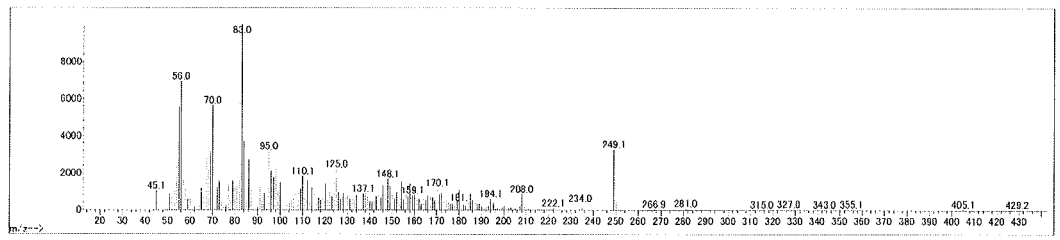
FIG. 10 shows a mass spectrum at the retention time of 7.737 min in a subject analysis step for Sample 1.

Similarly, the mass spectrum for Sample 1 shown in FIG. 10 has a peak at the m/z value of 249.1. Thus, the peak and the m/z value correspond to those of the mass spectrum for the crosslinking aid alone. Furthermore, the mass spectrum for Sample 1 also has peaks at the m/z value of 125.0, the m/z value of 83.0, and the m/z value of 70.0, as in the mass spectrum for the crosslinking aid alone shown in FIG. 9. Therefore, it can be determined that the mass spectrum includes the peaks of the triallyl isocyanurate used as the crosslinking aid and the decomposition products thereof.

Figure 11:
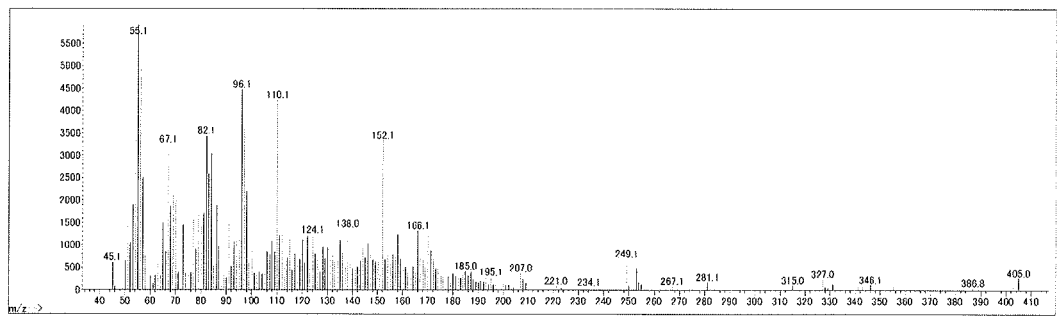
FIG. 11 shows a mass spectrum at the retention time of 7.737 min in a subject analysis step for Sample 3.

Similarly, the mass spectrum for Sample 3 shown in FIG. 11 has a peak at the m/z value of 249.1, and it can be determined that the mass spectrum includes the peaks of the triallyl isocyanurate used as the crosslinking aid and the decomposition products thereof.

Furthermore, regarding Sample 4 and Sample 5, it was possible to detect the remaining crosslinking aid by the same method.

Figure 12:
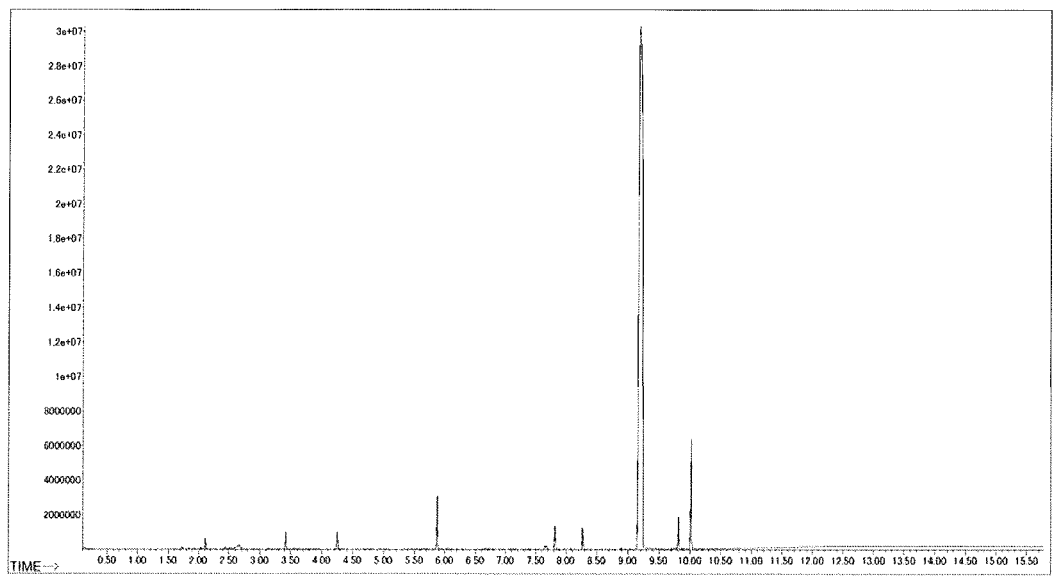
FIG. 12 is a chromatogram obtained in a standard analysis step for a crosslinking aid (trimethylol propane triacrylate) alone.

FIG. 12 shows a chromatogram for the crosslinking aid (trimethylol propane triacrylate) alone obtained in the standard analysis step for Sample 5.

As described above, by the method for detecting a residual crosslinking aid according to the present invention, it was possible to detect the crosslinking aid remaining in Sample 1 of a crosslinked resin molded body.

REFERENCE SIGNS LIST

S11 subject heating step
S12 subject analysis step
S13 detection step
S21 standard heating step
S22 standard analysis step

The invention claimed is:

1. A method for detecting a residual crosslinking aid in a crosslinked resin molded body, the method comprising:
    a subject heating step in which a crosslinked resin molded body is heated at a temperature of 500° C. or higher and 700° C. or lower for a time of 3 seconds or more and 30 seconds or less;
    a subject analysis step in which gas chromatographic analysis is performed on a gas generated in the subject heating step;
    a detection step in which an unreacted crosslinking aid is detected on the basis of a peak originating from a residual crosslinking aid in a chromatogram obtained in the subject analysis step;
    a standard heating step in which the crosslinking aid alone is heated under the same conditions as those in the subject heating step; and
    a standard analysis step in which chromatographic analysis is performed on a gas generated in the standard heating step,
    wherein, in the detection step, among peaks in the chromatogram obtained in the subject analysis step, a peak with a retention time equal to a retention time of a peak originating from the crosslinking aid in a chromatogram obtained in the standard analysis step is considered as the peak originating from the residual crosslinking aid.

2. The method for detecting a residual crosslinking aid according to claim 1, wherein the crosslinking aid is a monomer or oligomer having two or more double bonds other than aromatic rings in its structure.

3. The method for detecting a residual crosslinking aid according to claim 1, wherein the crosslinking aid is triallyl cyanurate or trimethylol propane triacrylate.

4. The method for detecting a residual crosslinking aid according to claim 1, wherein the crosslinked resin molded body has, as a main component, a polyamide, polyolefin, polyester, olefin-based resin, ester-based resin, styrene-based resin, fluororesin, or vinyl chloride resin.

* * * * *